(12) United States Patent
Grubbe et al.

(10) Patent No.: US 10,384,010 B2
(45) Date of Patent: Aug. 20, 2019

(54) MOTORIZED DRUG DELIVERY DEVICE WITH CHARGING SAFETY FEATURE

(71) Applicant: Novo Nordisk A/S, Bagsvaerd (DK)

(72) Inventors: Mikkel Schouenborg Grubbe, Hilleroed (DK); Mads Moeller, Hundested (DK); Carsten Schau Andersen, Valby (DK); Thomas Soerensen, Bagsvaerd (DK); Jesper Hoeholt, Melby (DK); Steffen Mews, Bagsvaerd (DK); Pete Brockmeier, Copenhagen V (DK); Bjoern Gullak Larsen, Birkeroed (DK)

(73) Assignee: Novo Nordisk A/S, Bagsvaerd (DK)

( * ) Notice: Subject to any disclaimer, the term of this patent is extended or adjusted under 35 U.S.C. 154(b) by 160 days.

(21) Appl. No.: 15/104,469

(22) PCT Filed: Dec. 16, 2014

(86) PCT No.: PCT/EP2014/078070
§ 371 (c)(1),
(2) Date: Jun. 14, 2016

(87) PCT Pub. No.: WO2015/091555
PCT Pub. Date: Jun. 25, 2015

(65) Prior Publication Data
US 2016/0331901 A1 Nov. 17, 2016

(30) Foreign Application Priority Data
Dec. 17, 2013 (EP) .................................... 13197594

(51) Int. Cl.
*A61M 5/20* (2006.01)
*A61M 5/315* (2006.01)
(Continued)

(52) U.S. Cl.
CPC ............ *A61M 5/2053* (2013.01); *A61M 5/20* (2013.01); *A61M 5/24* (2013.01);
(Continued)

(58) Field of Classification Search
CPC .. A61M 2005/2073; A61M 2005/2093; A61M 2005/3126; A61M 2005/31588;
(Continued)

(56) References Cited

U.S. PATENT DOCUMENTS 5,588,950 A 12/1996 Sano et al.
6,514,230 B1 2/2003 Munk et al.
(Continued)

FOREIGN PATENT DOCUMENTS

JP H06197875 A 7/1994
JP H08280612 A 10/1996
(Continued)

OTHER PUBLICATIONS

EP13153132.9, filed Jan. 29, 2013, priority document for WO2014118105.

*Primary Examiner* — Quynh-Nhu H. Vu
(74) *Attorney, Agent, or Firm* — Wesley Nicolas (57) ABSTRACT

Drug delivery device adapted to receive a drug-filled cartridge comprises a piston drive member for expelling a dose of drug from a loaded cartridge, a motor for driving the piston drive member, a rechargeable electric power source, an electrical connector allowing an external connector of a power source to be connected for recharging the power source, and a controller for controlling operation of the motor. The controller is adapted to detect a condition indicative of an external power source being connected to the electrical connector and subsequently disable the expelling assembly to thereby prevent that drug can be expelled from (Continued)

a loaded cartridge when an external power source has been connected to the electrical connector.

6 Claims, 6 Drawing Sheets

(51) Int. Cl.
*A61M 5/24* (2006.01)
*A61M 5/31* (2006.01)

(52) U.S. Cl.
CPC .... *A61M 5/31546* (2013.01); *A61M 5/31576* (2013.01); *A61M 2005/2073* (2013.01); *A61M 2005/2093* (2013.01); *A61M 2005/3126* (2013.01); *A61M 2005/31588* (2013.01); *A61M 2205/14* (2013.01); *A61M 2205/50* (2013.01); *A61M 2205/502* (2013.01); *A61M 2205/52* (2013.01); *A61M 2205/8206* (2013.01); *A61M 2205/8237* (2013.01)

(58) Field of Classification Search
CPC .......... A61M 2205/14; A61M 2205/50; A61M 2205/502; A61M 2205/52; A61M 2205/8206; A61M 2205/8237; A61M 5/20; A61M 5/2053; A61M 5/24
See application file for complete search history.

(56) References Cited

U.S. PATENT DOCUMENTS

| | | | |
|---|---|---|---|
| 7,193,521 | B2 | 3/2007 | Moberg et al. |
| 8,287,514 | B2 | 10/2012 | Miller et al. |
| 8,641,672 | B2 | 2/2014 | Yodfat et al. |
| 9,339,605 | B2 | 5/2016 | Wimpenny et al. |
| 2002/0096543 | A1 | 7/2002 | Juselius |
| 2009/0146609 | A1 | 6/2009 | Santos |
| 2011/0218502 | A1 | 9/2011 | Iio et al. |
| 2011/0306927 | A1 | 12/2011 | Watanabe et al. |
| 2012/0029433 | A1 | 2/2012 | Michaud et al. |
| 2012/0296269 | A1* | 11/2012 | Blomquist .......... G06F 19/3468 604/66 |
| 2013/0079708 | A1* | 3/2013 | Wimpenny .......... A61M 5/002 604/65 |

FOREIGN PATENT DOCUMENTS

| | | |
|---|---|---|
| JP | 2011517581 A | 6/2011 |
| JP | 2013523200 A | 6/2013 |
| WO | 2011117704 A2 | 9/2011 |
| WO | 2013184784 A1 | 12/2013 |
| WO | 2014118105 A1 | 8/2014 |
| WO | 2014118106 A1 | 8/2014 |
| WO | 2014118109 A1 | 8/2014 |
| WO | 2014118110 A1 | 8/2014 |
| WO | 2015091555 A1 | 6/2015 |

* cited by examiner

MOTORIZED DRUG DELIVERY DEVICE WITH CHARGING SAFETY FEATURE

CROSS-REFERENCE TO RELATED APPLICATIONS

This application is a 35 U.S.C. § 371 National Stage application of International Application PCT/EP2014/078070 (published as WO 2015/091555), filed Dec. 16, 2014, which claims priority to European Patent Application 13197594.8, filed Dec. 17, 2013.

The present invention generally relates to a motorized drug delivery device adapted to receive a drug-filled cartridge and subsequently expel a dose therefrom. The drug delivery device comprises a power source adapted to be recharged from an external power supply.

BACKGROUND OF THE INVENTION

In the disclosure of the present invention reference is mostly made to the treatment of diabetes by subcutaneous drug delivery, however, this is only an exemplary use of the present invention.

The most common type of durable drug delivery devices adapted to receive a drug-filled cartridge and expel a set dose therefrom are driven by manual means or by a spring energized during dose setting, the cartridge being of the type comprising an axially displaceable piston having an initial proximal position. Subcutaneous drug delivery takes place via an injection needle arranged in fluid communication with the cartridge. The device may be pen-formed or in the form of a more box-shaped so-called doser. In order to improve convenience, user-friendliness and provide additional features, e.g. detection and storing of expelling data, drug delivery devices have been provided with electrically driven means, typically in the form of an electronically controlled motor driving a piston rod through a gear arrangement, e.g. as shown in U.S. Pat. No. 6,514,230 and US 2011/306927. The same arrangement is also used in infusion pumps, e.g. as shown in U.S. Pat. No. 7,193,521. To drive the motor and the supporting electronics such a drug delivery device is provided with a power source in the form of one or more "batteries" (electric cells). In an infusion pump the batteries are typically standard disposable batteries whereas in a motorized pen-type drug delivery device the battery is typically build-in and rechargeable, e.g. as used in the "pendiq" digital insulin pen manufactured by Diamesco Co. Ltd, Daejeon, Korea.

However, a build-in battery will typically be charged using an external charger adapted to be connected to a wall power outlet supplying e.g. 110 or 220 volts. If the connection to an external charger is done via a wired connection, there may be a potential risk of electrocution to a user if the user were to attempt to use the device while the device was still connected to the external device. For instance, an internal fault or fluid leakage within the drug delivery device could bypass the electrical insulation measures of the device and allow direct connection between the power source and the user.

Addressing this issue, US 2013/0079708 which is hereby incorporated by reference discloses rechargeable drug delivery devices configured such that an administration of the drug is prevented while the device is connected to an external charger. More specifically, US 2013/0079708 discloses a number of different designs in which it is physically prevented that a charger can be connected to the drug delivery device unless the device is in a "mechanical state" in which drug delivery is not possible.

Having regard to the above, it is an object of the present invention to provide a motorized drug delivery device which provides a high degree of safety in a cost-effective and convenient way.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in accordance with a first aspect of the invention a drug delivery device is provided comprising a drug-filled cartridge or a compartment adapted to receive a drug-filled cartridge, the cartridge comprising a body portion, an axially displaceable piston, and a distal outlet portion adapted to be arranged in fluid communication with a flow conduit. The drug delivery device further comprises an expelling assembly comprising a rechargeable electric power source, an electrical connector allowing an external connector of a power source to be connected for recharging the power source, an axially displaceable piston drive member adapted to engage the piston of a loaded cartridge, a motor for driving the piston drive member in a distal direction to thereby expel drug from a loaded cartridge, and a controller for controlling operation of the motor. The controller is adapted to detect a condition indicative of an external power source being connected to the electrical connector and subsequently disable the expelling assembly to thereby prevent that drug can be expelled from a loaded cartridge when an external power source has been connected to the electrical connector.

By such an arrangement a motorized drug delivery device is provided which provides a high degree of safety in a cost-effective and convenient way. Further, by providing the safety feature primarily in the electric and electronic domain a high degree of freedom of design for the drug delivery device in general is assured.

The controller may be adapted to detect the physical presence of a connected connector. Alternatively, the controller may be adapted to detect that a voltage is supplied to the electrical connector. The controller may be in the form of e.g. a micro-controller, a customizable microcontroller or an ASIC. The controller may comprise one or more ICs and may be used in combination with additional electronic circuitry providing the desired functionality for the device.

The expelling assembly may comprise setting means, allowing a user to set a dose of drug to be expelled, and the controller may be adapted to disable the setting means when an indicative condition is detected. The setting means may be in the form of a setting device, e.g. one or more user input keys, or a wired or wireless receiver adapted to receive setting input from an external source such as a PC or a smartphone.

The drug delivery device may further comprise a display, the controller being adapted to control the display to indicate that the expelling assembly has been disabled when an indicative condition is detected.

The drug delivery device may be provided as an assembly in combination with an external power supply comprising an external connector adapted to be received in the drug delivery connector.

The electronic controller may be adapted to store dose data representing one or more pre-set doses and subsequently control the motor to move the drive member to thereby expel an amount of drug corresponding to a pre-set dose. The drug delivery device may further comprise communication means allowing dose setting data to be received from an external device. By this arrangement a given amount of drug to be expelled can be set and stored in the drug delivery device by external means, this providing a drug delivery device which is both simple and easy to use when a dose corresponding to a stored value is to be delivered.

The controller may comprise a clock and be adapted to store dose setting data representing at least two pre-set doses, each pre-set dose being associated with a time period of the day and/or week, the controller being adapted to control the motor to move the drive member to thereby expel a stored dose amount according to the actual time.

The drug delivery device may be provided with a first switch for actuating the device between an idle condition and an activated condition, and a second switch for actuating the controller to expel an amount of drug corresponding to a set dose, the controller being adapted to display a stored dose amount when the device is actuated from the idle to the activated condition, the stored dose amount representing a pre-set dose. The first switch may be activated when a protecting cap is removed.

In a further aspect of the invention an electronically controlled device is provided comprising an actuator, a rechargeable electric power source, an electrical connector allowing an external connector of a power source to be connected for recharging the power source, and a controller for controlling operation of the actuator. The controller is further adapted to detect a condition indicative of an external power source being connected to the electrical connector and subsequently disable the actuator to thereby prevent that the actuator is operated when an external power source has been connected to the electrical connector.

In this way a battery operated device is provided in which a given functionality provided by an actuator is disabled when the device is attached to an external power supply for recharging the battery.

In a yet further aspect of the invention a method of operating a drug delivery device is provided, the method comprising the steps of (i) providing a rechargeable drug delivery device comprising a motorized drug expelling assembly, the drug delivery device having an electrical connector allowing an external connector of a power source to be connected for recharging the drug delivery device, (ii) detecting a condition indicative of an external power source being connected to the electrical connector, and (iii) in case an indicative condition is detected, disable the expelling assembly to thereby prevent that drug can be expelled from the drug delivery device when an external power source has been connected to the electrical connector.

As used herein, the term "drug" is meant to encompass any flowable medicine formulation capable of being passed through a delivery means such as a cannula or hollow needle in a controlled manner, such as a liquid, solution, gel or fine suspension, and containing one or more drug agents. Representative drugs include pharmaceuticals such as peptides (e.g. insulins, insulin containing drugs, GLP-1 containing drugs as well as derivates thereof), proteins, and hormones, biologically derived or active agents, hormonal and gene based agents, nutritional formulas and other substances in both solid (dispensed) or liquid form. In the description of the exemplary embodiments reference will be made to the use of insulin containing drugs, this including analogues thereof as well as combinations with one or more other drugs.

BRIEF DESCRIPTION OF THE DRAWINGS

In the following exemplary embodiments of the invention will be further described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The term "assembly" does not imply that the described components necessarily can be assembled to provide a unitary or functional assembly during a given assembly procedure but is merely used to describe components grouped together as being functionally more closely related.

Figure 1:
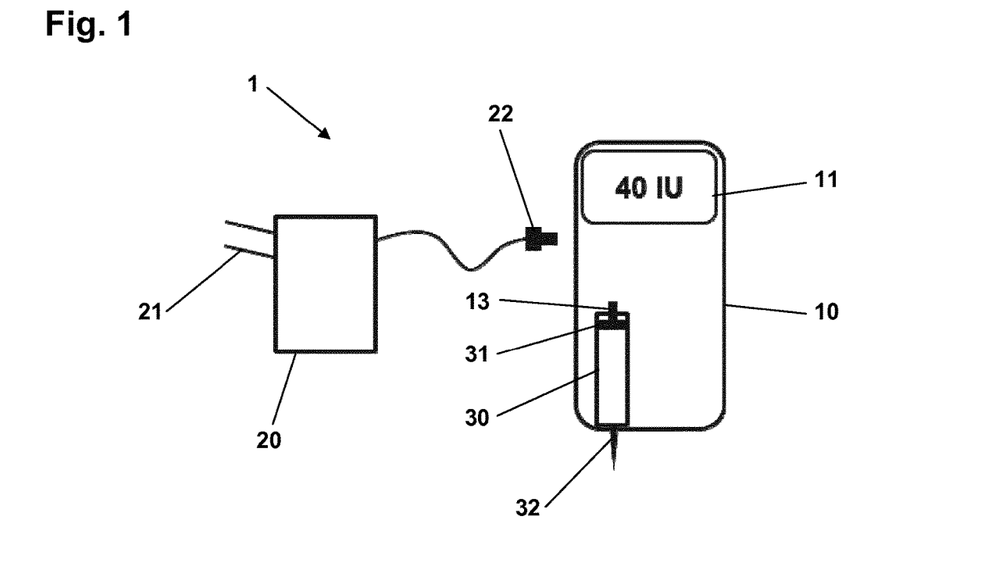
FIG. 1 shows a drug delivery device and charger assembly.

Referring to FIG. 1 an assembly 1 is disclosed comprising a drug delivery device 10 and an external wall charger 20. More specifically, the drug delivery device is in the form of an electronically controlled motorized drug delivery device 10 adapted to receive a drug-filled cartridge 30 comprising an axially displaceable piston 31 and an outlet to which a needle assembly 32 adapted for subcutaneous infusion can be mounted. The device comprises a housing, a compartment adapted to receive and hold the cartridge, an electronically controlled expelling assembly comprising a motor 14 for driving an axially displaceable piston drive member 13 adapted to engage the piston of a loaded cartridge, a controller 40 coupled to the expelling assembly and configured to control the expelling assembly to move the piston in a distal direction to thereby expel drug from a loaded cartridge, an electrical energy source 15 for the controller and the expelling assembly, user-operated input means for setting a desired dose of drug to be expelled, as well as a display 11 adapted to show a set dose, e.g. "40 IU" as shown.

A more detailed description of a drug delivery device suitable as a platform for embodiments of the present invention will be given below with reference to FIGS. 7-9. Other suitable drug delivery device platforms are known, e.g. in the form of a compact doser incorporating a flexible piston rod as disclosed in U.S. Pat. No. 6,514,230, a pen-formed device incorporating a rigid piston rod as disclosed in US 2011/306927 or an infusion pump as disclosed in U.S. Pat. No. 7,193,521 which are all hereby incorporated by reference.

In the embodiment of FIGS. 1-4 the energy source is in the form of a rechargeable "battery" which is charged from an external power supply via a female connector 12, the shown external power supply being in the form of a portable charger 20 having a mains inlet 21 and a male outlet connector 22 adapted to be received in the device female connector 12. The connector may e.g. be a micro USB connector which would also allow data to be transferred between the drug delivery device and an external device, e.g. a PC. For example, log data for expelled drug doses could be transferred from the device, just as settings, e.g. an allowed maximum dose, could be transferred to the device.

Figure 2:
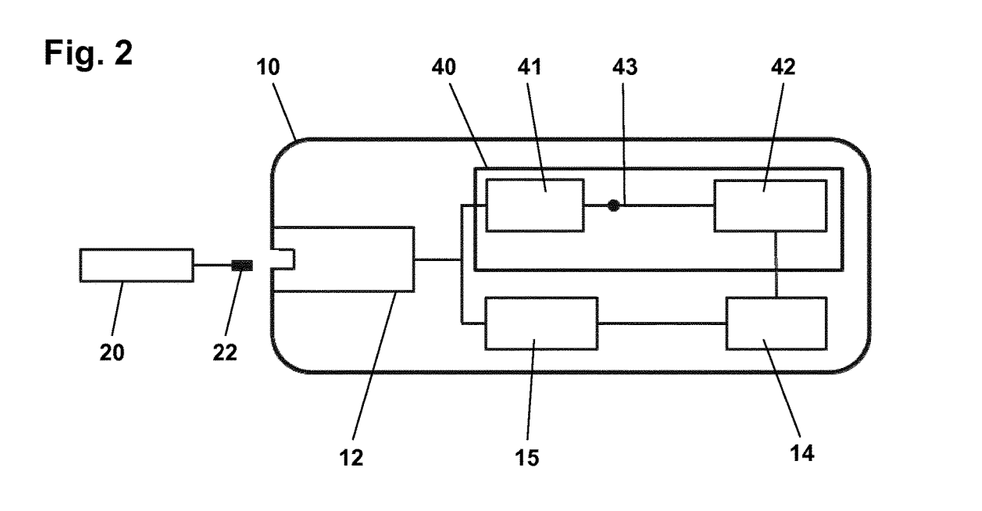
FIG. 2 shows schematically components of the assembly of FIG. 1.

The controller is in the form of micro controller (MCU) 40 which in the shown embodiment comprises a power handling unit 41, a dosing controller unit 42 for controlling the motor and a switch 43 there between. Although the units and the switch are shown schematically as separate components they merely represent functions implemented by programming on the general MCU platform. The controller may be associated with a receiver and/or transmitter allowing the device to communicate with an external source, e.g. by wireless means with a smartphone. In this way a log of expelled doses could be transferred to a smartphone or the smartphone could be used to conveniently enter pre-set dose sizes.

Figure 3:
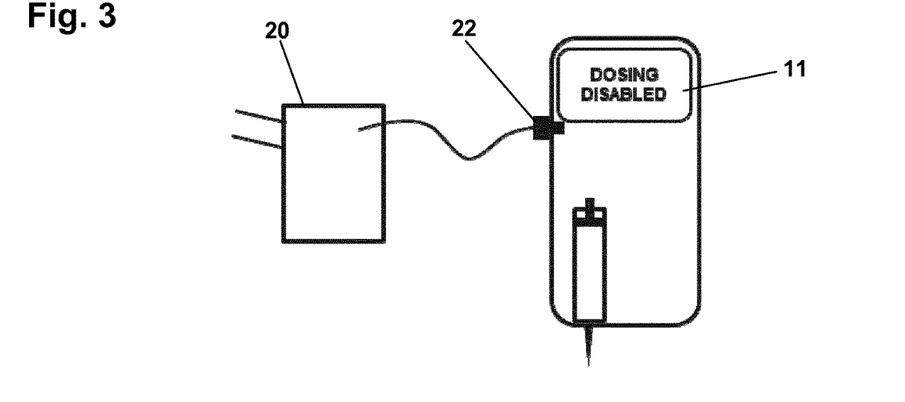
FIG. 3 shows the assembly of FIG. 1 in a connected state.
Figure 4:
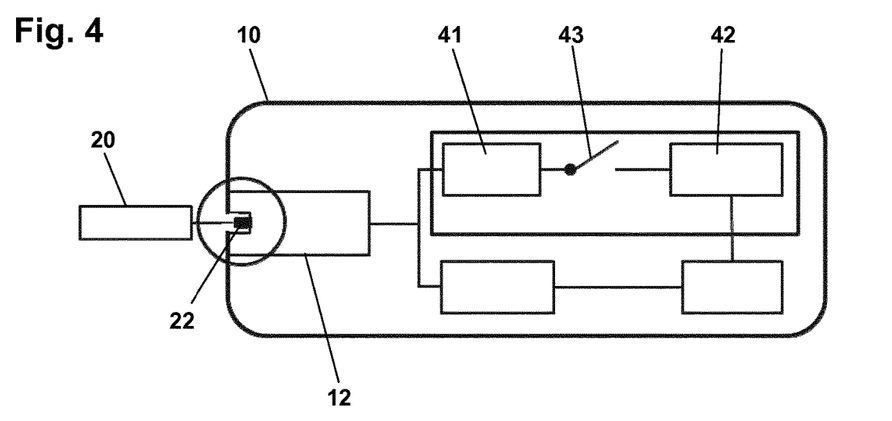
FIG. 4 shows schematically components of the assembly of FIG. 1 in a connected state.

Turning to FIGS. 3 and 4 a situation of use is shown in which the charger 20 has been connected to the drug delivery device 10. When the power handling unit 41 detects that a connector has been inserted in the device connector the dosing controller 42 is disabled preventing the motor from being actuated and thus a dose of drug to be expelled when a connector has been inserted. Preferably also the dose setting user interface is disabled just as the display 11 is controlled to indicate that dosing is disabled as shown in FIG. 3. In this way it is prevented to a high degree that the user will try to make an injection while an external power source is connected to the device.

Figure 5:
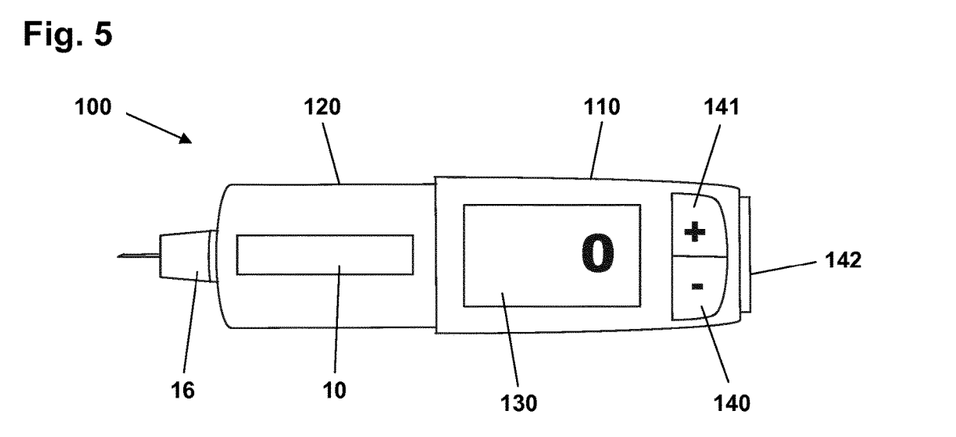
FIG. 5 shows schematically a pen-formed drug delivery device.

FIG. 5 shows schematically an embodiment of a pen-formed drug delivery device 100 adapted to receive a disposable pre-filled drug cartridge, the device comprising a body portion 110 with an electronically controlled motor driven expelling mechanism, a rechargeable battery, a charging connector (not shown), a cartridge holder portion 120 adapted to receive and hold a drug filled cartridge 10, means allowing a needle assembly 16 to be mounted in fluid communication with the cartridge (may be formed as part of the disposable cartridge), a display 130 adapted to show a set dose to be expelled, up-down setting keys 140, 141 allowing a user to set or adjust a desired dose, and actuation means 142 to actuate the expelling mechanism to expel an amount of fluid drug from the cartridge corresponding to the set dose size, e.g. units of insulin (IU). In the shown embodiment the display is adapted to show text, however, alternatively the display may be a simple 7-segment display which could be adapted to display one or more additional symbols. A cap (not shown) is provided to cover the cartridge portion and a needle if attached. The cap may be used to turn on the device when the cap is removed.

Figure 6A:
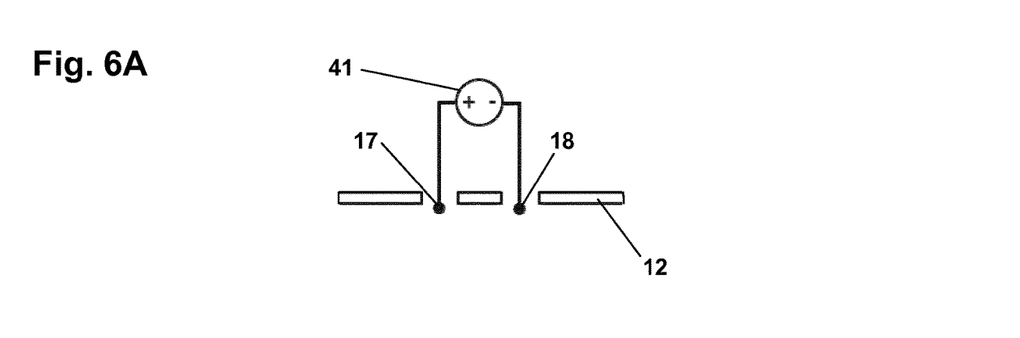
FIGS. 6A and 6B show a first embodiment of a set-up for detection of an inserted connector.
Figure 6B:
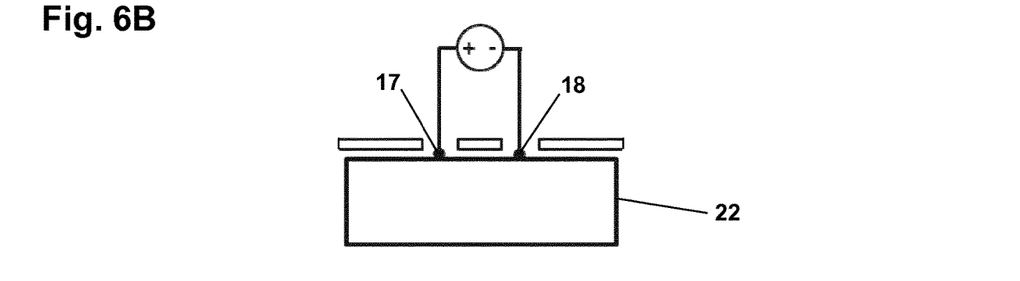

Turning to FIGS. 6A and 6B a first embodiment of a set-up for detection of an inserted connector is shown schematically. The device female connector 12 (shown in part) is provided with a pair of contact points 17, 18 connected to the power handling unit 41 and adapted to engage an electrically conducting outer surface of an inserted male connector 22. Correspondingly, when an electrical connection is detected between the two contact points 17, 18 this indicates that a connector 22 has been inserted as shown in FIG. 6B. As merely the physical presence of a connector is detected, dosing will be disabled also when no voltage is or can be supplied to the device. The latter may be the case if a data-only connector is inserted.

Figure 7A:
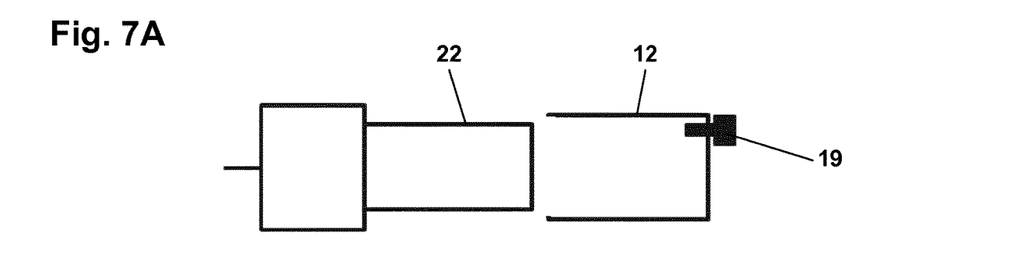
FIGS. 7A and 7B show a second embodiment of a set-up for detection of an inserted connector
Figure 7B:
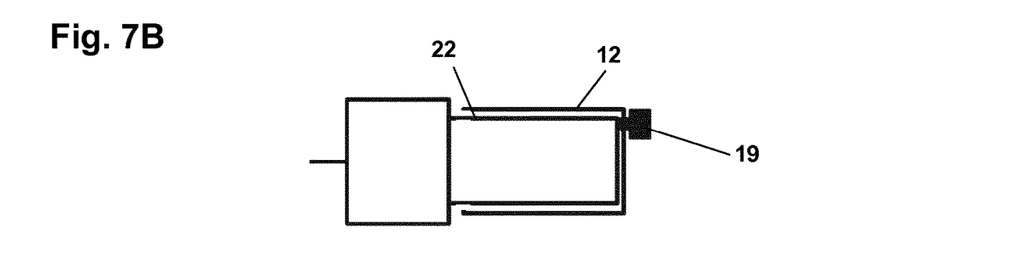

In FIGS. 7A and 7B a second embodiment of a set-up for detection of an inserted connector is shown schematically. The device female connector 12 is provided with a micro switch 19 connected to the power handling unit and adapted to be actuated by an inserted male connector 22. In this way the detection of an inserted connector is less dependent upon the specific design of the male connector. Correspondingly, when the micro switch is actuated as shown in FIG. 7B this indicates that a connector has been inserted.

Figure 8:
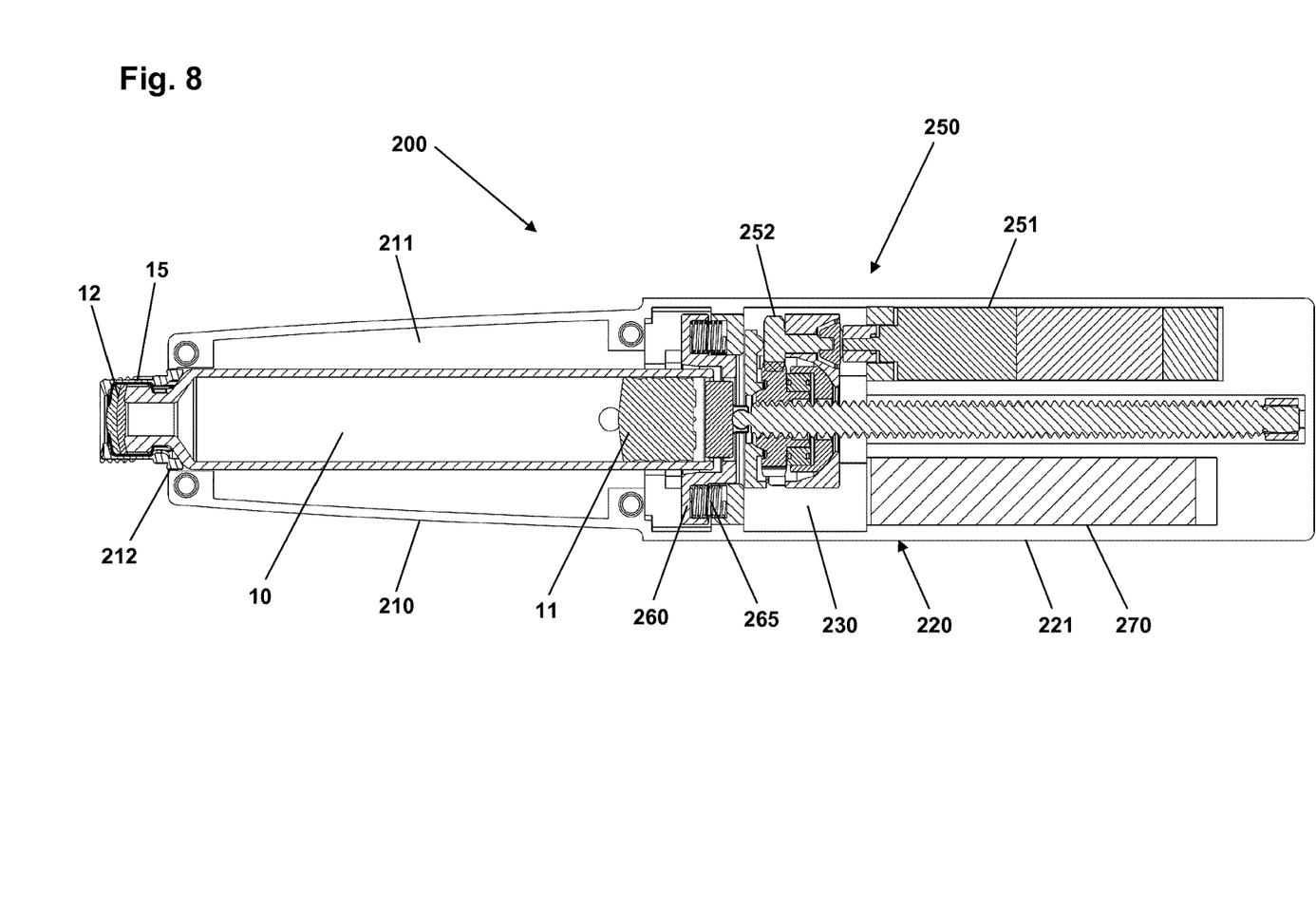
FIG. 8 shows a first embodiment of a drug delivery device platform.

Turning to FIG. 8 a first embodiment 200 of a drug delivery device suitable as a platform for embodiments of the present invention will be described. More specifically, the device comprises a cap part (not shown) and a main part having a proximal body or drive assembly portion 220 with a housing 221 in which a motorized drug expelling assembly 250, electronic controller and communication circuitry 270 and an electric power source are arranged, and a distal cartridge holder portion 210 with a compartment 211 in which a drug-filled cartridge 10 is arranged and retained in place. The cartridge comprises a generally cylindrical main portion with an axially displaceable piston 11 and a distal outlet portion 12 comprising a needle-penetrable septum. The cartridge is further provided with distal coupling means in the form of a needle hub mount 15 having, in the shown example, an external thread adapted to engage an inner thread of a corresponding hub of a needle assembly. The cartridge may for example contain an insulin, a GLP-1 or a growth hormone formulation. The device further comprises dose setting means allowing a user to set a dose of drug to be expelled as well as a display for showing the set dose, e.g. as shown in FIGS. 1 and 5.

In the shown embodiment the device is designed to be loaded by the user with a new cartridge through a distal receiving opening 212 in the cartridge holder assembly, the cartridge holder comprising closure means (not shown) operatable by a user between an open position in which a cartridge can be inserted respectively removed, and a closed position in which an inserted cartridge is held in place. The closure means may be of the same type as described with respect to FIG. 9 below. In order to axially position the cartridge, the device comprises a seat member 260 adapted to receive the proximal end of the cartridge, the seat member being biased in the proximal direction by springs 265 thereby forcing the cartridge into contact with the closure means.

When incorporating an embodiment of the present invention in the platform device of FIG. 8, the necessary controller functionality could cost-effectively be integrated in the electronic controller circuitry 270.

Figure 9:
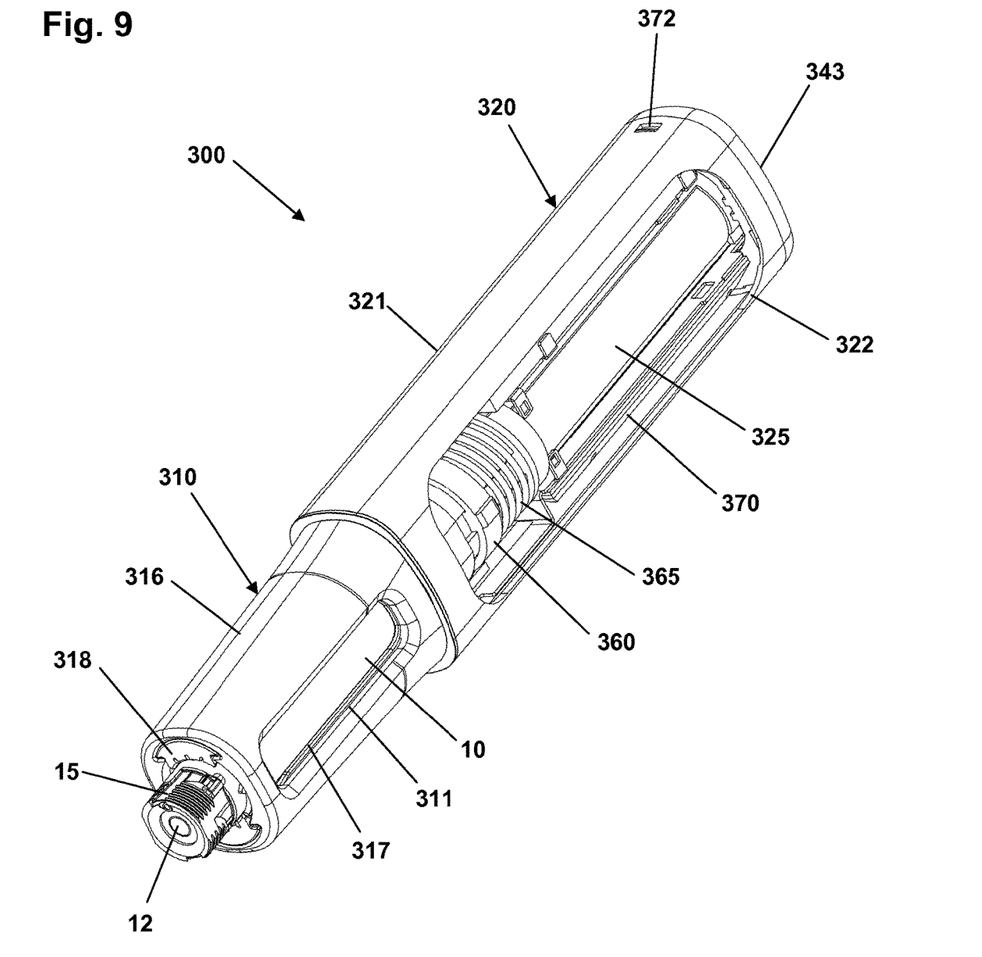
FIGS. 9 and 10 show a second embodiment of a drug delivery device platform.

Turning to FIG. 9 a second embodiment 300 of a drug delivery device suitable as a platform for embodiments of the present invention will be described. More specifically, the device comprises a cap part (not shown) and a main part having a proximal body or drive assembly portion with a housing 321 in which a drug expelling mechanism and associated control and communication electronics are arranged, and a distal cartridge holder assembly 310 forming a compartment in which a drug-filled transparent cartridge 10 can be arranged and retained in place, the cartridge holder assembly comprising a pair of opposed inspection openings 311. The housing comprises an opening 322 adapted to receive a display frame member (not shown) in which a LCD as well as user input keys are mounted, e.g. as shown in FIG. 5. With the frame member removed, it can be seen that the device comprises a generally tubular chassis member 325, in which a generally cylindrical expelling assembly is mounted (see below). The device further comprises a control and communication assembly 370, a bias assembly comprising a bias member 360 and a spring 365, and a proximal release button 343. The control and communication assembly may comprise a wireless transmitter/receiver. An external charger can be received in female connector 372. The connector may be e.g. a micro USB connector which would also allow data to be transferred between the drug delivery device and an external device, e.g. a PC. A pair of dose setting input keys (not shown) serves to manually set a desired dose of drug shown in the LCD and which can then be expelled when the release button 90 is actuated. The device is designed to be loaded by the user with a new cartridge through a distal receiving opening in the cartridge holder assembly.

The cartridge 10 comprises a cylindrical body portion, a distal outlet portion 12 with a distal needle-penetrable septum, and an axially displaceable piston having a proximal surface allowing a piston driver forming part of the expelling mechanism (see below) to engage the piston. The cartridge may for example contain an insulin, a GLP-1 or a growth hormone formulation. The cartridge is provided with distal coupling means in the form of a needle hub mount 15 having, in the shown example, combined thread and bayonet coupling means, each being adapted to engage an inner thread or bayonet coupling means of a corresponding hub of a needle assembly. The shown exemplary hub mount further comprises a circumferential flange with a number of distally facing pointed projections serving as a coupling means for the cartridge holder assembly as will be described in more detail below. A hub mount of the shown type is described in U.S. Pat. No. 5,693,027. Alternatively the needle hub mount may be formed as part of the cartridge holder, e.g. in the form of a "split" hub mount having two parts arranged on each side of the gripping shoulders.

As shown, the cartridge holder assembly 310 has the same general appearance as a traditional cartridge holder which is detachably coupled to the housing by e.g. a threaded coupling or a bayonet coupling and into which a new cartridge can be received as well as removed through a proximal opening, i.e. it comprises no additional user operated release or locking means. Instead, what appears merely to be the cartridge holder per se is in fact user operated coupling means in the form of an outer rotatable tubular actuation sleeve 316 operated by the user to control movement of cartridge holding means in the form of an inner cartridge holder member 317 to thereby open and close gripping shoulders 318 configured to grip and hold a cartridge. More specifically, each gripping shoulder is provided with a plurality of gripping teeth spaced circumferentially to provide a plurality of gaps, each tooth having a triangular configuration with a proximally oriented pointed end, thereby creating a plurality of gaps having a distally oriented pointed configuration, this allowing the above-described distally facing pointed projections on the cartridge to be received between the teeth to thereby serve as a gripping means when the cartridge holding means has been moved into engagement with the cartridge. In this way an easy-to-use front loaded drug delivery device is provided which appears as a traditional rear loaded device and which is also actuated by rotational movement to mount and remove a cartridge, the resemblance providing for ease of acceptance and adaptation among users accustomed to traditional types of rear loaded drug delivery devices.

When it is time to mount a new cartridge the outer tube member 316 is rotated e.g. 90 degrees by which action the gripping shoulders 318 are moved distally and slightly outwards, this allowing the mounted cartridge to be removed. For ease of operation the cartridge may be moved distally a certain distance as the shoulders are moved, e.g. by engagement with arms forming the gripping shoulders and/or by additional spring means providing a biasing distally directed force (see below). Depending on the design of the locking and actuation mechanism the gripping shoulders may be able to be left in the open position or they may be retracted automatically as the outer tube member is rotated backwards by return spring means. Whether or not a spring is provided the cartridge holder may be provided with locking means allowing the outer tube member to be securely parked in either the open or closed position, e.g. by a rotational snap lock. When a new cartridge is inserted the drive expelling means has to be in a state allowing a new cartridge with a proximally positioned piston to be inserted. An exemplary embodiment providing this functionality will be described below.

Figure 10:
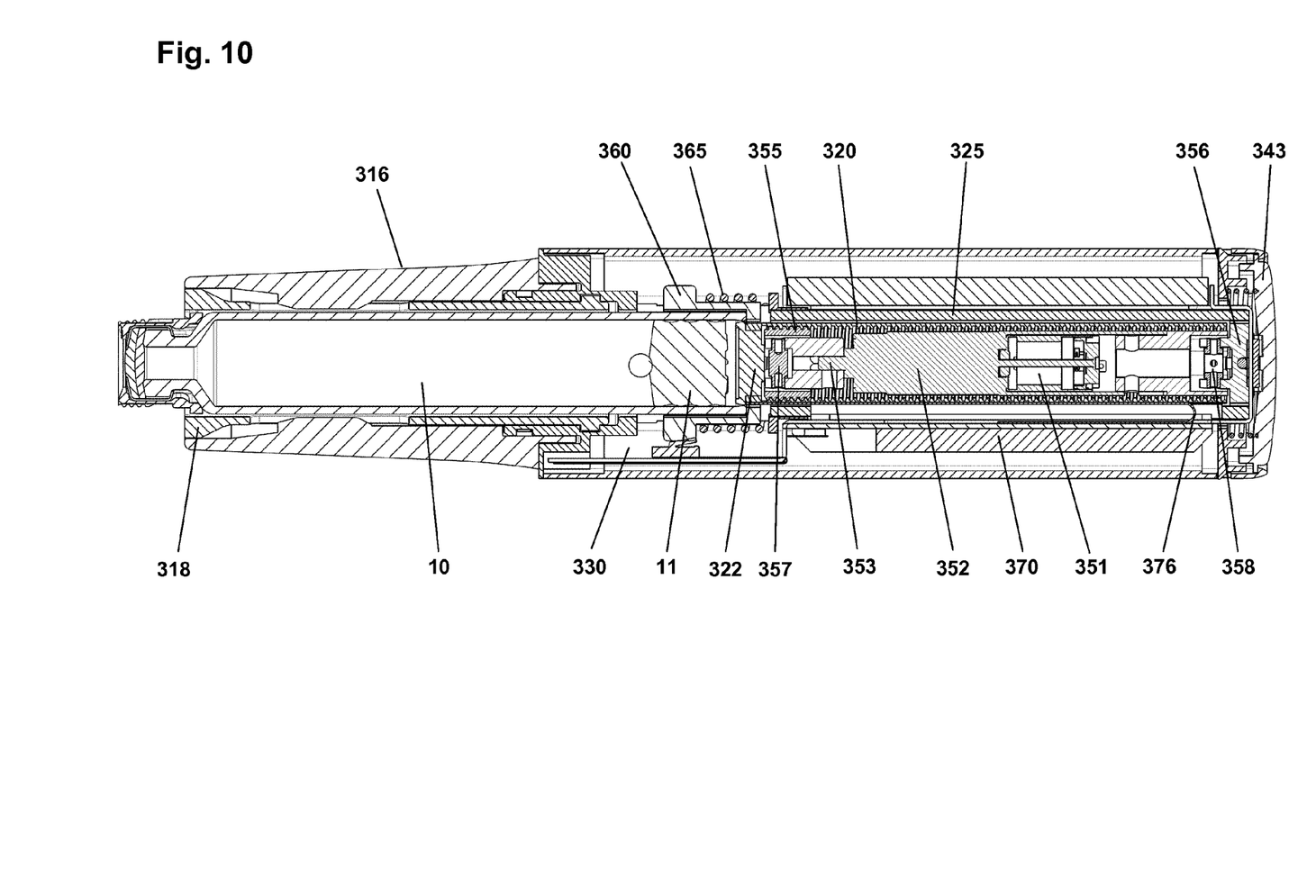

Turning to FIG. 10 a cross-sectional view of the drug delivery device 300 of FIG. 9 is shown with a mounted cartridge 10 and with the piston tube 320 (see below) in a fully retracted position. More specifically, the actuation sleeve 316 has been rotated to its operational position and the cartridge holder gripping shoulders 318 have been retracted to their closed position thereby retracting the cartridge to its fully inserted position, thereby also moving the bias member 360 proximally against the bias of the spring 365. In the shown embodiment a cartridge switch 375 is hereby being actuated, this providing a signal to the device controller that two actions can be assumed to have taken place: (i) a cartridge has been inserted and (ii) the cartridge holder has been closed, this initiating that the drive head is moved distally into contact with the cartridge piston. In the shown embodiment it is contemplated that detection of contact between the drive head and the piston is detected by electronic sensor means arranged in the drive head, e.g. using proximity detection as disclosed in WO 2013/144152.

FIG. 10 also shows the expelling assembly in greater detail. More specifically, the expelling assembly is in the form of a motor-in-piston assembly comprising an interior motor and gearbox drive assembly mounted axially and rotationally locked to the proximal end of the chassis, and an outer axially displaceable piston tube 320 with a distal drive head 322 adapted to engage the piston 11 of a loaded cartridge, the piston tube comprising a number of guide projections adapted to non-rotationally engage corresponding guide means of the chassis.

The motor-gear drive assembly comprises a tubular main portion 310 composed of a proximal motor assembly 351 and a distal gearbox assembly 352 having a rotatable drive shaft 353 defining a z-axis of rotation. The assembly further comprises a distal cylindrical drive member 355 having an outer thread adapted to be arranged in engagement with the piston drive tube inner thread. At the proximal end a disc-formed chassis connector 356 is arranged. In the shown embodiment the drive assembly is provided with flexible joints in the form of a distal universal joint 357 arranged between the drive shaft and the drive member and a proximal universal joint 358 arranged between the motor assembly proximal portion and the chassis tube proximal portion. A corresponding drive assembly is described in greater detail in patent application EP 14166859.0 which is hereby incorporated by reference.

A number of further details can be seen in FIG. 10. The release button 343 is received in the housings proximal opening with a spring providing a proximally directed biasing force on the button. A flexible ribbon 376 with a plurality of conductors is arranged with a U-bend between the electronics portion 370 and the sensors (not shown) arranged in the piston head, this allowing the piston tube and piston head to travel axially with the U-bend moving correspondingly.

When incorporating an embodiment of the present invention in the platform device of FIGS. 9 and 10, the necessary controller functionality could cost-effectively be integrated in the control assembly 370.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. Drug delivery device, comprising:
   a drug-filled cartridge, or a compartment adapted to receive the drug-filled cartridge, the drug-filled cartridge comprising a body portion, an axially displaceable piston, and a distal outlet portion adapted to be arranged in fluid communication with a flow conduit,
   an expelling assembly comprising:
      a rechargeable electric power source,
      an electrical connector allowing an external connector of an external power source to be connected for recharging the power source,
      an axially displaceable piston drive member adapted to engage the piston of the drug-filled cartridge,
      a motor for driving the piston drive member in a distal direction to thereby expel drug from the drug-filled cartridge, and
      electronic controller for controlling the motor,
   wherein the electronic controller is adapted to detect an indicative condition of the external power source being connected to the electrical connector and subsequently disable the expelling assembly to thereby prevent that drug can be expelled from the drug-filled cartridge when the external power source has been connected to the electrical connector.

2. Drug delivery device as in claim 1, wherein the electronic controller is adapted to detect a physical presence of a connected connector.

3. Drug delivery device as in claim 1, wherein the electronic controller is adapted to detect that a voltage is supplied to the electrical connector.

4. Drug delivery device as in claim 1, wherein the expelling assembly comprises setting structure allowing a user to set a dose of drug to be expelled, and the electronic controller is adapted to disable the setting structure when the indicative condition is detected.

5. Drug delivery device as in claim 1, further comprising a display, the electronic controller being adapted to control the display to indicate that the expelling assembly has been disabled when the indicative condition is detected.

6. Drug delivery device as in claim 1 in combination with the external power source comprising the external connector adapted to be received in the electrical connector to thereby charge the rechargeable electric power source.

* * * * *